United States Patent [19]
Lubell et al.

[11] Patent Number: 4,566,461
[45] Date of Patent: Jan. 28, 1986

[54] HEALTH FITNESS MONITOR

[76] Inventors: Michael Lubell, 1504 Jefferson St.; Stephen Marks, 603 Sunderland Rd., both of Teaneck, N.J. 07666

[21] Appl. No.: 466,671

[22] Filed: Feb. 15, 1983

[51] Int. Cl.$^4$ .............................................. A61B 5/02
[52] U.S. Cl. ................................... 128/668; 128/689; 128/700; 128/707; 364/417
[58] Field of Search ............... 128/668, 707, 700, 706, 128/687-690, 670; 364/417

[56] References Cited

U.S. PATENT DOCUMENTS

| | | | |
|---|---|---|---|
| 4,281,663 | 8/1981 | Pringle | 128/707 |
| 4,343,315 | 8/1982 | O'Leary | 128/689 |
| 4,367,752 | 1/1983 | Jimenez et al. | 128/707 X |
| 4,434,801 | 3/1984 | Jimenez et al. | 128/707 X |

OTHER PUBLICATIONS

De Crosta, "Fitness—The Pulse Monitors You Love to Hate", *Bicycling*, Apr. 1982, p. 24, ff.
Fichtner, "The Beat Goes On with Pulse Monitor", Sunday Miami Herald, Mar. 30, 1980, p. 4G.
Goldstein, "Computer Counts Calories", Sunday Miami Herald, Mar. 30, 1980, p. 3F.
Amertec 110 Pulsemeter brochure.
Coach—Bicycle Adapter Kit instructions, 1982.
*Fitness Testing and Categories*, pp. 29, 30.
Aastrand, "Reduction in Maximal Oxygen Uptake with Age", Journal of Physiology, Nov. 1973, pp. 649-653.
SPORTPAGES Catalog, Vacation 1979 issue, p. 19.
*Runner's World*, Jul. 1979, p. 33.
*The Runner*, Jul. 1979, (advertizing page).
"Biometrics" advertizing release.
"Smart Heart Monitor", Advertizement.
Palmer et al., *Bicycling*, Feb. 1983, Adv.
"Optimize Your Exercise" and Bikomputer, Adv. page.
*Machine Design*, (undated), p. 12.
"Sharper Image", adv. (Jul. 1979).
JS & A, Heart Computer, 1980.
"Finally, A Computer . . . Exercise Program", (undated).
"No Dogging it with this Computer Watch", *Engineering News* (undated).
Walter, "Fitness Equipment Paces Sporting Goods", *Industry Week*, Dec. 14, 1981, p. 110.
*Markline*, Adv. (undated).
Respironics, Exersentry brochure (undated).
Advice, p. 30 (undated).
Pulseminder brochure (undated).
Amerec ERM-101 brochure (undated).

*Primary Examiner*—William E. Kamm
*Assistant Examiner*—John C. Hanley
*Attorney, Agent, or Firm*—Bruns and Wall

[57] ABSTRACT

A heart rate monitor device suitable for use in monitoring aerobic exercise training, automatically calculates a fitness parameter for a subject by monitoring the subject's heart rate and pacing the subject through a submaximal exercise stress test protocol. A microprocessor in the device is fed data peculiar to the individual subject, and then generates pacing signals to produce audible tones or beeps. The stride frequency, or rate of the tones varies at intervals so that the subject can exercise by running at progressively faster speeds. At the point of exhaustion, or maximum heart rate, the subject's maximal oxygen uptake capacity is calculated, based on the elapsed time, and is displayed as a fitness parameter. The subject's exercise level is automatically monitored based on his or her exercise heart rate, maximum heart rate, and rest heart rate.

17 Claims, 6 Drawing Figures

GRAPHICS

| # | Label | Graphic |
|---|---|---|
| 1 | SYSTEM |  "US" 30, "MR" 31 |
| 2 | SEX – FEMALE/MALE |  ♀ 41, ♂ 40 |
| 3 | HEIGHT |  42 |
| 4 | WEIGHT |  43 |
| 5 | DISTANCE |  46 |
| 6 | BICYCLE |  35 |
| 7 | TEST PROTOCOL |  44 |
| 8 | H.R. |  36 |
| 9 | RESTING H.R. |  33 |
| 10 | RUNNING PACE (SPEED) |  47 |
| 11 | CALORIES CONSUMED |  48 |
| 12 | PACER |  45 |
| 13 | RECOVERY RATE | 🕐 34 |
| 14 | ENTER | "E" |
| 15 | RUN PAUSE | "R"   "P" |
| 16 | VO$_2$ MAX |  37, 33 |

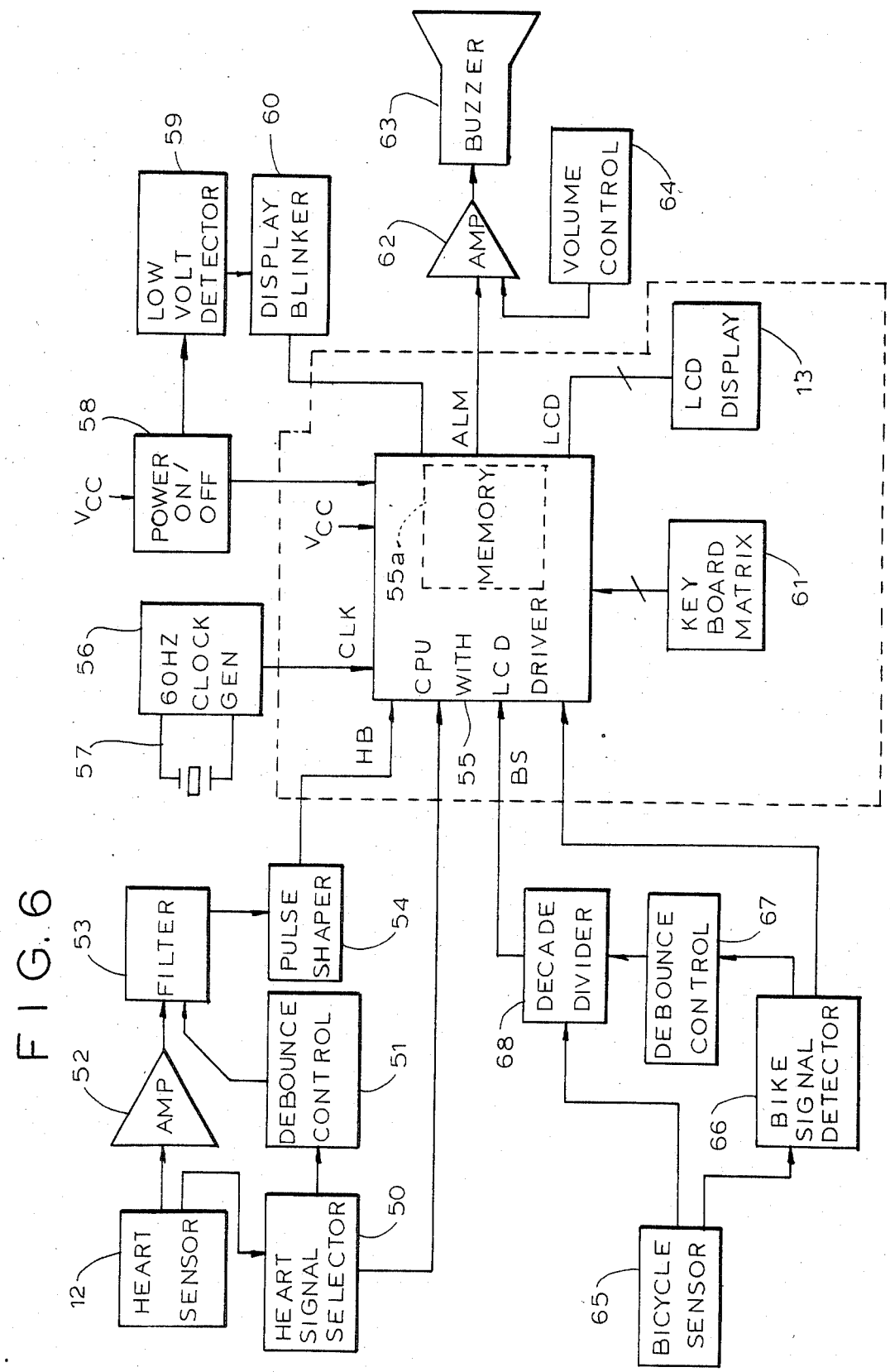

HEALTH FITNESS MONITOR

This invention relates to health and fitness monitors, such as heart rate monitors and the like. This invention is more particularly directed to a device for monitoring the exercise training of an animate subject, such as a human runner or cyclist, a race horse, or other being whose fitness level can be determined directly or indirectly from measurement of heart rate.

Devices for measuring the aerobic fitness of an individual subject and monitoring the level of fitness during exercise training or therapy normally require the determination of the subject's heart rate. This is done both at rest and during active exercise. These heart rate devices typically provide a display of a heart rate, in beats per minute (BPM) on a meter or display, such as a liquid crystal display (LCD).

A generally accepted principle of aerobic training, at least with human subjects, is that during exercise the heart rate should be maintained within a range of above about 60 percent and below about 80 percent of the subject's maximum heart rate. Accordingly, heart rate monitors or fitness monitors are often provided with alarms which will sound when the subject's exercise level is such as to put his or her heart rate above the 80 percent level or below the 60 percent level. This helps the subject keep his exercise stress level within what is regarded as the fitness training range.

It has been previously proposed to construct fitness monitors including a pedometer to count the number of strides when subject is running. From this the fitness monitor calculates the distance run by multiplying the number of steps times the subject's stride length. A clock or chronometer provides elapsed time in hours, minutes, and seconds, and the average speed can be derived from these and expressed in miles per hour or kilometers per hour. In a typical such device, the number of calories consumed by the subject is automatically estimated (roughly) using the elapsed exercise time and the subject's average speed.

Recently, the capacity of the subject's cardiovascular system to bring oxygen to the body tissues has been determined to be perhaps the most meaningful index of aerobic fitness. As this fitness index is usually expressed in terms of the volume of oxygen taken up by the cardiovascular system, per kilogram of body weight, per minute, this fitness index is commonly referred to as the maximal oxygen uptake, or $VO_{2max}$. Generally, this fitness index $VO_{2max}$ is higher, the greater the level of fitness is for a given individual. For example, a sedentary thirty year old male who routinely does little or no exercise may have a fitness index $VO_{2max}$ of about 30–35 milliliters of oxygen per kilogram of body weight per minute. On the other hand, a well-trained thirty-year-old male distance runner may have a fitness index $VO_{2max}$ of about 70 milliliters per kilogram per minute. As a general proposition, this fitness index declines with age, and, for the same fitness level, is slightly lower for women than for men.

The application of maximal oxygen uptake $VO_{2max}$ as an index of fitness, is discussed, e.g., in Astrand and others, for example, in the Journal of Physiology, November 1963.

For any given individual, the maximal oxygen uptake $VO_{2max}$ can be estimated, with an accuracy of about 10 to 15 percent, from that individual's oxygen consumption at submaximal work loads.

In one previously-proposed fitness monitoring system, this fitness index $VO_{2max}$ was calculated by having the subject exercise, at whatever speed he or she desired, for a period of twelve minutes. Preferably, this exercise was constituted by running. Then, at the end of the twelve minute period, the fitness $VO_{2max}$ was derived from a simple, look-up table, based on the distance covered in that twelve minutes.

This system has the advantage of being simple to administer, but is not universally applicable. That is, it is not accurate for subjects of a range of ages or fitness levels. In fact, the original data for this system were based only on the performance of a homogenous group of male U.S. Air Force recruits who were already in reasonably good physical shape. This twelve-minute-run approach to calculation of maximal oxygen uptake levels is not particularly accurate for other groups, as it does not recognize that subjects may vary greatly in physique, muscle tone, or many other physiological variables, from one individual to another. For that reason, this approach was not particularly useful in determining the fitness level for individuals somewhat unlike these male Air Force recruits, such as cardiac recovery patients or persons at the beginning level of a fitness training program.

In addition, previous heart rate monitors and fitness monitors normally require manual entry of resting heart rate, minimum exercise heart rate, maximum exercise heart rate, and a previously-calculated fitness index or maximal oyxgen uptake level $VO_{2max}$. That is, there is no provision in the existing or previously proposed heart rate monitor devices for programming the device automatically and measuring the subject's fitness automatically.

Some previously proposed fitness monitors provided pacing tones to provide a footfall cadence for runners to pace themselves at various speeds. However, there is no provision in such fitness monitors to accomodate variability in stride length, which increases as the subject's running speed increases. This variability occurs because for a portion of the runners stride, both feet are out of contact with the ground. The out-of-contact portion of the stride increases in length as the running speed increases.

Accordingly, it is an object of this invention to provide a heart rate monitor and/or fitness monitor device which avoids the drawbacks of the previously proposed devices, and automatically calculates an appropriate fitness parameter (e.g., maximal oxygen uptake level or $VO_{2max}$) by automatically pacing the subject through a straightforward training protocol.

It is another object of this invention to provide such a heart rate monitor device which automatically calculates and displays the resting heart rate, exercise heart rate, distance covered, and calories consumed for the individual subject during an exercise training session.

It is yet another object of this invention to provide such a heart rate monitor device which is adaptable to either running (jogging) or cycling, with the latter being performed either on a mobile bicycle or stationary exercise bicycle.

It is a still further object of this invention to provide such a heart rate monitor which is portable, and is easily programmed by a user, which can be the subject himself or herself, or the subject's trainer.

In accordance with a favorable aspect of this invention, a heart rate monitor device is provided for monitoring the heart rate of an animate subject during exercise training. A heart beat sensor worn on the subject senses his, her, or its heartbeat. The heart rate monitor also includes data entry means for entering selected data peculiar to the subject, display means for displaying the entered selected data and also displaying one or more fitness parameters calculated on the basis of the entered selected data and the detected heart beats of the subject. At the core of the heart rate monitor is a microprocessor which stores the entered data and the heart rate data calculated from the detected heart beats and calculates the fitness parameter or parameters based on the entered data and the heart rate data. Within the microprocessor, a timer is included for measuring the heart rate of the subject on the basis of the detected heart beats. An indicator, such as an audible alarm device or a visual display, provides the subject with an indication of the level of exercise.

The above mentioned fitness parameters include at least the maximal oxygen uptake $VO_{2max}$ as a fitness index, the determination of which is carried out as follows:

(1) The weight M of the subject, the height H of the subject, and the subject's sex are entered on the data entry means and are stored in the microprocessor as the selected data.

(2) Using the heart beat sensor, the microprocessor measures the heart rate of the subject while at rest and stores that heart rate as a resting heart rate $HR_R$.

(3) The indicator then provides indications, such as pacing tones, to establish an exercise cadence (such as a running stride frequency) for the subject at a predetermined pacing rate so that the subject can follow a graded submaximal exercise tolerance test. Data gathered from this test are used for deriving the subject's maximal oxygen uptake level $VO_{2max}$. In this exercise tolerance test, the exercise cadence is provided at a first, slow rate for a first period (e.g., three minutes), and at progressively faster cadences for corresponding successive periods (e.g., of three minutes), while the microprocessor continuously measures the heart rate of the subject while he, she, or it is exercising at the prescribed cadence.

(4) When the subject reaches a maximal heart rate $HR_M$, or when the subject reaches the point of exhaustion, whichever occurs first, the subject depresses a key on the device halting the test. Then the time T from the commencement of the exercise tolerance test until the maximum heart rate $HR_M$ is attained is provided from the timer of the microprocessor. The maximal oxygen uptake $VO_{2max}$ is determined according to the Van der Walt relationship, $VO_{2max} = aT + b$, where a and b are experimentally derived cooefficents.

(5) This derived value of $VO_{2max}$ is then displayed as the calculated fitness index, and is used to monitor the aerobic training of the subject.

In a preferred fitness index submaximal exercise test protocol, the subject, wearing the device, is paced to run at speeds of approximately four miles per hour for the first three minutes, and then at six miles per hour, eight miles per hour, ten miles per hour, twelve miles per hour, and fourteen miles per hour for the successive three minute intervals. Although the speed of four miles per hour (i.e. fifteen minutes per mile) can be walked by most persons without much trouble, the experimental data have been derived for running, and the subject should run, even at this relatively low speed.

The maximal heart rate, which is calculated at 220 minus the subject's age (where the subject is human) is used as the maximum heart rate.

The subject runs at the speed corresponding to the pacing tones provided by the fitness monitor device. These tones occur at cadences which increase each three minutes. When the subject reaches the point of exhaustion, of reaches his or her maximum heart rate $HR_M$, the exercise tolerance test is halted, and the subject pushes an appropriate key or push button on the device. Then, the subject's fitness index is calculated according to the Van der Walt relationship used for the running test:

If the total elapsed time T is less than seven minutes, the fitness $VO_{2max}$ is calculated according to the relationship:

$$VO_{2max} = 3.83T + 13;$$

but where the time T is between 7 and 18 minutes, the fitness index $VO_{2max}$ is calculated according to the relationship $$VO_{2max} = 2.33T + 24.$$

Here, T is expressed in minutes, and $VO_{2max}$ is expressed of milliliters of oxygen per kilogram of body weight per minute.

These values are applicable for men. For women, the value of $VO_{2max}$ would be reduced by about one-eighth.

This quantity $VO_{2max}$ is used in monitoring a program for the subject's fitness training.

Audio pacing tones, which can each represent a step at a running pace cadence or stride frequency SF, are provided to correspond to exercise at a rate selected for training. Preferably this stride frequency results in exercise stress a fraction ($\%VO_{2max}$) of the maximal oxygen uptake $VO_{2max}$ within a range of, e.g., 60-80%.

Also, the subject's submaximal oxygen uptake $VO_2$ can be continuously calculated. The fraction of maximal oxygen uptake ($\%VO_{2max}$) represents the exercise stress level for the individual subject. This can be calculated using the subject's exercise heart rate $HR_E$ and his or her previously calculated and stored values of rest heart rate $HR_R$ and maximal heart rate $HR_M$. This value ($\%VO_{2max}$) can be calculated according to the relationship:

$$(\% VO_{2max}) = \frac{HR - HR_R + 10}{HR_M - HR_R}$$

In a preferred embodiment, the heart rate monitor device can optionally be mounted on a bicycle or stationary exercise cycle. A speed sensor, which can be any of a variety of well-known sensing means, is mounted on a wheel of the bicycle or exercise cycle, and is plugged into the device. For example, a magnetic sensor could be readily applied for this purpose. This permits the subject to use the bicycle or exercise cycle for aerobic training exercise, and permits monitoring his or her exercise. In such case, the speed can be indicated directly on the LCD display of the monitor device.

Also, in a preferred embodiment, the actual submaximal oxygen uptake $VO_2$ is calculated at regular intervals (e.g., one minute intervals), and this parameter can be used to calculate caloric consumption during training for the particular subject.

The foregoing and many other objects, features, and advantages of this invention will become apparent from the ensuing description of a preferred embodiment of this invention to be described below with reference to the accompanying drawrngs While the description given below is of an exemplary embodiment intended for use with a human subject using running as the preferred training exercise, it is to be understood that a device embodying this invention could be suitably adapted for use when cycling, swimming, or some other exercise is the preferred training exercise. In such case, a suitable submaximal exercise test protocol could be used, in a controlled exercise environment. Furthermore, devices embodying this invention could be adapted for monitoring the training of non-human subjects, such as race horses or dogs.

In the drawings:

FIG. 6 is a schematic circuit diagram of the described embodiment of this invention.

Figure 1:
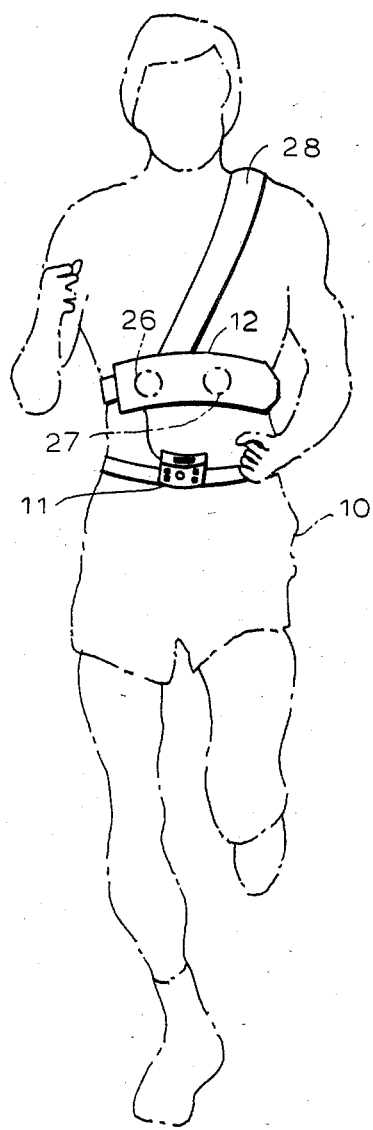
FIG. 1 is an environmental view of a human subject shown fitted with one embodiment of the device according to this invention.

With reference to the drawings, and initially to FIG. 1 thereof, a human subject 10 is shown fitted with a heart rate monitor 11 of this invention, here worn at the waist. Here, the subject 10 is an adult male, although the same device can be used as easily for women and children. An associated heart beat sensor 12 is worn on the subject's chest and furnishes heart beat pulse signals to the device 11.

Figure 2:
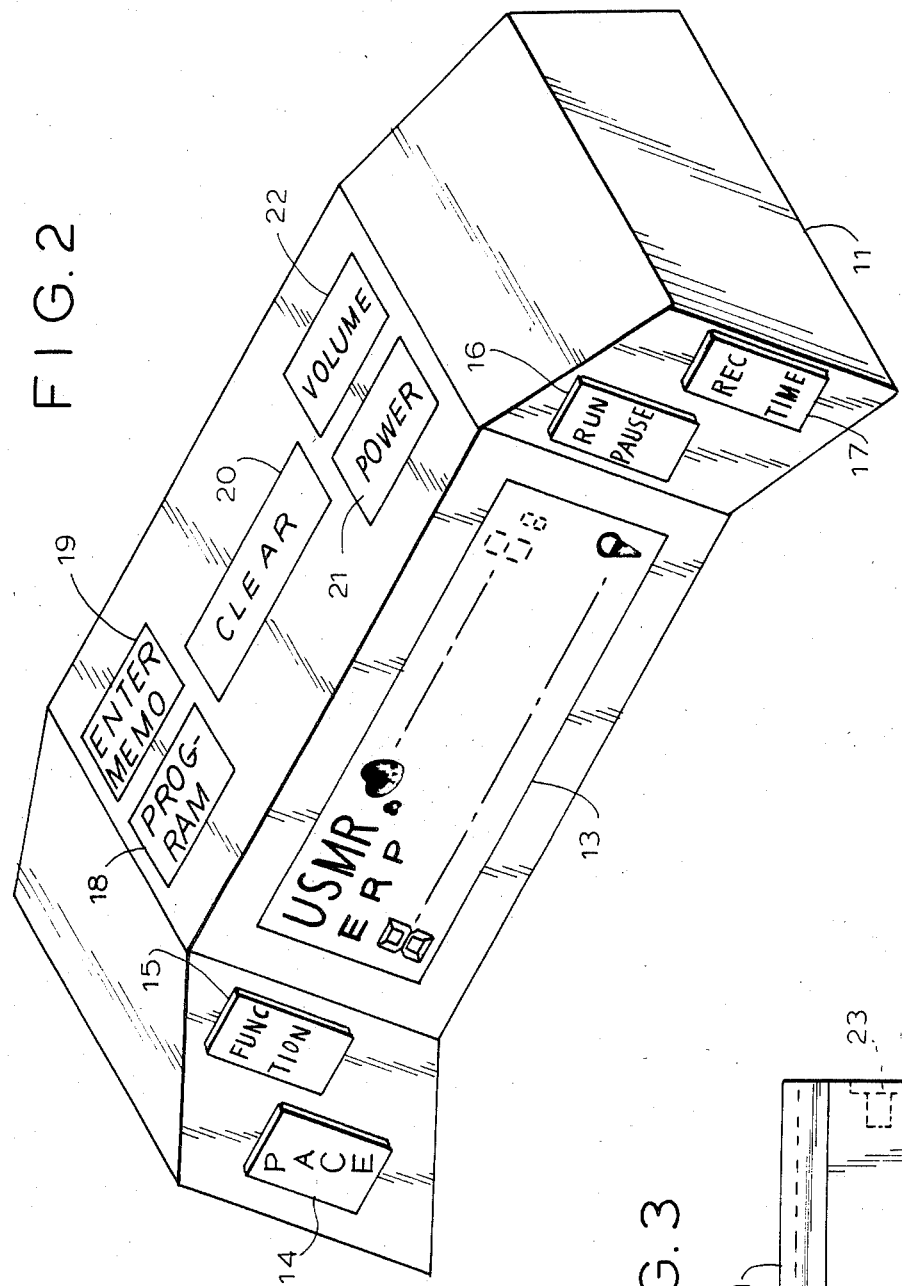
FIG. 2 is a perspective view of a heart rate fitness monitor according to one embodiment of this invention.
Figure 3:
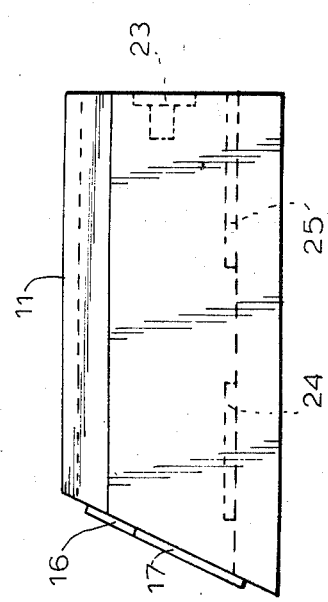
FIG. 3 is a side elevational view of a heart rate fitness monitor of this embodiment of the invention.

As shown in FIGS. 2 and 3, a front panel of the device 11 has a liquid crystal display (LCD) display panel 13 and a PACE push-button key 14, a FUNCTION key 15, a RUN/PAUSE key 16, and a RECOVERY/TIME key 17. A top panel of the device 11 has a PROGRAM push-button key 18, an ENTER/MEMO key 19, a CLEAR key 20, a POWER (on/off) key 21, and a VOLUME control key 22. A recessed socket 23 is provided on a back panel of the device 11 to receive a jack from the heart beat sensor 12. While not shown here, the device 11 also has a similar socket to accept another jack from a bicycle sensor, not shown, to be described later. A lower panel of the device 11 has a belt clip 24 for fitting a waist belt or cinch. A battery compartment cover 25 also on the lower panel of the device 11 covers a battery compartment.

Returning to FIG. 1, the heart beat sensor here has a pair of electrodes 26 and 27, as indicated by dotted lines, to contact the subject's skin and pick up the heart beats electrically. Also, an optional shoulder strap 28 can be provided to hold the heart beat sensor 12 in place while the subject is running.

It is noted here that for an equine heart rate fitness monitor, a similar arrangement would be used as the heart beat sensor 12, having a strap placed just behind the horse's front legs, preferably at the girth. In that case, one of the electrodes 26 would be disposed at the withers, and the other electrode 27 behind the knee.

Figure 4:
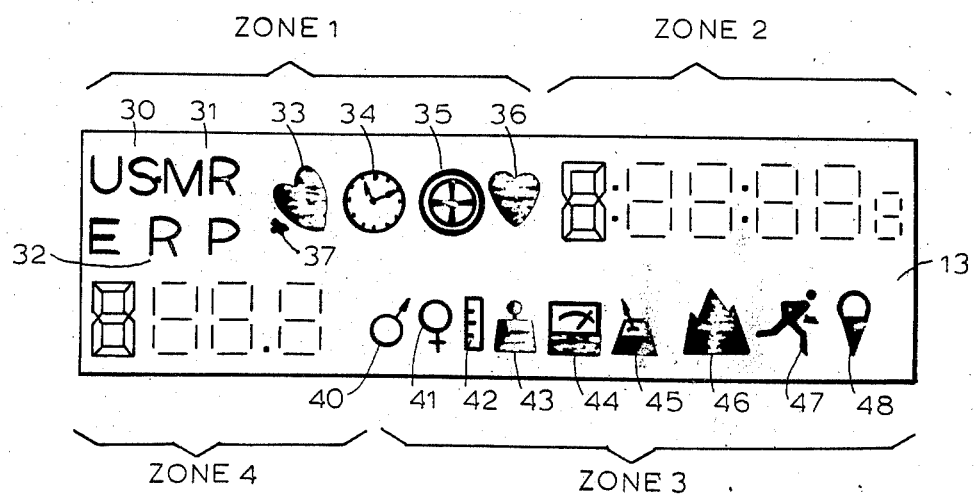
FIG. 4 is a plan view of the display panel of the embodiment of FIG. 2.
Figure 5:
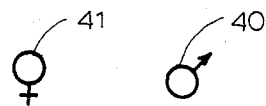
FIG. 5 is a chart showing and explaining the graphics used on the display panel of FIG. 4.
Figure 5:
Figure 5:
Figure 5:
Figure 5:
Figure 5:
Figure 5:
Figure 5:
Figure 5:
Figure 5:
Figure 5:
Figure 5:
Figure 5:

The preferred arrangement of the LCD display panel 13 is shown in FIG. 4, with the graphics depicted thereon being explained with reference to FIG. 5.

A first zone, i.e., ZONE 1 of the panel 13 contains a first and second measuring system indications 30 and 31. The indication 26 is displayed if units such as miles, pounds, and inches are used, while the indication 31 is displayed if the international system of units, i.e., kilometers, kilograms, and centimeters, is used.

Also in ZONE 1 is a program status field 32, in which are displayed letters "E", "P", and "R" to indicate Enter, Pause, and Run, respectively.

Further, in ZONE 1 there are a resting heart indication 33 which is displayed to indicate a resting heart rate; a clock face 34 to indicate heart rate recovery time, a bicycle wheel indication 35 to indicate that a bike mode is selected (this is displayed automatically when the bicycle jack is plugged in), a heart indication 36 to indicate the exercise heart rate, and a further indication 37 which appears as a cloud below the resting heart rate indication 33 to indicate the display of maximal oxygen uptake $VO_{2max}$. The heart indication 36 flashes for each heart beat of the subject 10 provided the device 11 is on and the sensor 12 is plugged in.

In another zone, ZONE 2, of the display 13 is a stopwatch or chronometer, i.e., an elapsed time display showing hours, minutes, seconds, and tenths of second.

In a further zone, ZONE 3, are a series of graphic displays to indicate the mode of the device. Male and female display indicators 40 and 41 are selected according to the particular gender of the subject 10. A ruler 42 indicates that the subject's height is to be entered. A weight indication 43 is displayed when the subject's weight is to be entered. A gauge or meter graphic indication 44 is displayed to indicate commencement of a test mode, in which a submaximal exercise test protocol is carried out. To indicate pacing rate or cadence, a metronome graphic 45 is displayed; when the distance that has been run is to be displayed, a mountain figure graphic 46 appears; to indicate running speed (in minutes per mile or minutes per kilometer) a running stick-figure graphic 47 appears; and when total calories consumed during exercise is to be displayed, a ice-cream-cone-shaped graphic 48 appears.

A fourth zone, ZONE 4, has a numeric display of four decimal digits. It is here that resting heart rate, exercise heart rate, speed, distance, and caloric consumption are displayed, in connection with the appropriate graphics from ZONE 1 or ZONE 3. It is also here that the subject's height and weight are displayed when entered using the keys 18, 19.

The electronic circuitry for the device 11 is shown generally in FIG. 6. Here heart beat indications are provided as electrical pulses from the heart beat sensor 12 to a heart signal selector 50 which is followed by a debounce control circuit 51, and are also furnished through an amplifier 52 to a filter 53, which is connected to the debounce control circuit 51. The latter is followed by a wave shaper 54, which provides appropriately shaped heart beat pulses HB to a microprocessor circuit 55, here formed of a central processing unit and a driver for the LCD display 13. This microprocessor also includes an internal memory storage area 55a, and counter circuits which can be used functionally as a timer. The heart beat indications are also delivered directly from the heart beat signal selector 50 to the microprocessor 55. A 60 Hz clock generator 56, controlled by a crystal 57, provides clocking signals CLK to the microprocessor 55. A power on/off circuit, controlled by the key 21, couples battery supply voltage $V_{cc}$ to the microprocessor 55, and also supplies this voltage to a low voltage detector 59, which causes the display 13 to blink when the battery voltage $V_{cc}$ is below a predetermined level.

In the preferred embodiment, the voltage $V_{cc}$ is supplied from three AA dry cells at a nominal 4.5 volts. The detector 59 causes the display 13 to flash when the voltage $V_{cc}$ drops below about 3 volts.

This voltage $V_{cc}$ is also supplied unswitched directly to the microprocessor and is used to maintain certain data in the memory 55a, such as the subject's height, weight, and maximal oxygen uptake $VO_{2max}$, between uses.

A keyboard matrix 61 interfaces between the various keys 14 to 20 and the microprocessor 55, while the latter furnishes display drive signals LCD to the liquid crystal display 13.

Audio alarm signals ALM are furnished from the microprocessor 55 through an audio amplifier 62 to an audio transducer 63. These are used to pace the exercise of the subject 10 and also to indicate when the subject's stress level ($\%VO_{2max}$) is outside the training range. A volume control circuit 64, controlled by the VOLUME key 22, controls the gain of the amplifer 62.

Also provided in association with the microprocessor 55 is a bicycle speed detection circuit. In this circuit, a bicycle sensor 65, preferably disposed on or in proximity to the front wheel of the bicycle or exercise cycle, provides pulses, e.g., at the rate of one pulse for each bicycle wheel revolution, to a bike signal detector 66, which furnishes a pulse signal directely to the microprocessor 55 and also furnishes a signal through a debounce control circuit 67 to a decade (i.e., divide-by-ten) divider. The latter, which also has an input receiving the sensor signal from the bicycle sensor 65 provides bicycle pulse signals BS to the microprocessor 55.

As mentioned briefly above, the microprocessor 55 is also provided with counter circuitry and the latter is used for counting the heart beat signals HB for predetermined intervals of time to determine the subject's heart rate. Preferably, at least one further counter is provided in the microprocessor 55. If the bicycle sensor 65 is plugged in, this further counter will count occurrences of the bike speed signal BS, for use in determining cycling speed and cycling distance. If the bicycle sensor 65 is not plugged in, the additional counter stores cadence pulses corresponding to steps that the subject has taken during exercise, and can be used for computing distance traveled during running that is carried out for training exercise.

Favorably these counters can be formed of partitions within the memory 55a.

The operation of the heart rate monitor device 11 of this invention can be explained as follows:

The subject 10 mounts the device 11 securely on a belt or on other appropriate mounting means and then places it on his or her waist. Then, the subject dons the heart beat sensor 12, and plugs the same into the appropriate socket on device 11.

Initially, in ZONE 1, the program status indicator 32 will indicate E and P and the indications 30 and 31 will be displayed alternately. E always is displayed during a programming mode. The subject selects either the U.S. system (mile, pounds, inches) or the metric system (kilometers, kilograms, centimeters) by depressing the ENTER/MEMO key 19 when the appropriate system indication 30 or 31 is being flashed. For the sake of example, we will assume that it is desired to select U.S. units, that is, mile, pounds, inches, etc.

Then, E and P are displayed in the program status indicator 32, and the male and female indications 40 and 41 are alternately displayed. The appropriate sex is indicated by pressing the enter memo key 19 when the appropriate symbol 34 or 35 is being flashed. For purposes of illustration, we will assume that the subject is male. Thus, at this time, the symbols 30 and 34 are permanently displayed.

Thereafter, the graphic display 42 shows in zone 3, and the subject 10 depresses the PROGRAM key 18. As a result, the four digits in zone 4 count up from 000 to 299 until the subject's own height is reached. Then, the subject releases the PROGRAM key 18 and depresses the ENTER/MEMO key 19 to enter the data into the memory 55a. For example, if the subject is 5 feet 10 inches tall, the data entered would be "070".

Thereafter, the graphic symbol 43 is displayed, and the subject enters his weight (here in pounds) in a similar fashion.

At this time, the microprocessor 55 automatically calculates and stores the subject's resting heart rate by counting the pulses provided from the heart sensor 12 for a perscribed period, for example, six seconds. Then, this quantity is represented in ZONE 4, and the graphic symbol 33 is displayed in ZONE 1.

The submaximal exercise test protocol begins at this point with the program status indicators of field 32 in ZONE 1 showing E and P, and with the test mode graphic 38 displayed in ZONE 3. This protocol paces the subject 10 through a prescribed submaximal exercise program for calculating his fitness index, or maximal oxygen uptake $VO_{2max}$.

When the subject 10 is ready to begin the submaximal exercise test, he pushes the RUN/PAUSE key 16. Now the indicator R is displayed in the field 32. The cumulative time then is stored and is shown on the display in ZONE 2. Audible pacing tones are provided from the audio transducer 63 to pace the subject 10 at a running cadence or stride frequency SF.

In accordance with a preferred test protocol, these pacing tones are provided, at first, at a cadence corresponding to a running speed of 15 minutes per mile (i.e., four miles per hour), and, the subject 10 begins running in step with the pacing tones. This cadence is maintained for a period of three minutes, or until the subject 10 attains a maximal heart rate, or feels exhausted.

At the same time, the display graphic 36 flashes on and off with each beat of the subject's heart. As mentioned above this occurs at all times that the heart beat sensor 12 is in place and plugged in. The subject's heart beat rate, expressed in terms of beats per minute (BPM) is shown on the display on ZONE 4. This display is updated every six beats (or ten seconds), on a moving-average basis. The maximal heart rate $HR_M$ is determined by subtracting the age of the subject from 220. For example, if the subject is 30 years of age, the maximal heart rate would be 190 BPM.

After the first three minutes, the cadence SF for the pacer tone is speeded up to correspond to a running speed of six miles per hour (10 minutes per mile) and this cadence is maintained for the next three minutes. The cadence of the pacer tones is speeded up at successive three minute intervals to correspond to eight, ten, twelve, and fourteen miles per hour, in succession. However, only a person in superb athletic condition would be expected to run for three minutes at the fastest pace, as this corresponds to a speed of about 4½ minutes per mile, so the subject 10 would terminate the test at an appropriate earlier time.

At the point in the test protocol when the subject 10 attains his maximum heart rate, or simply becomes too exhausted to continue, he presses the ENTER/MEMO key 19. At this time, the maximum heart rate attained by the subject 10 is stored as the maximal heart rate $HR_M$, as is the elapsed time T shown in ZONE 2. This elapsed time T is used to compute the maximal oxygen uptake $VO_{2max}$ for the subject 10.

As has been mentioned previously, an individual's fitness index, or maximal oxygen uptake $VO_{2max}$ can be estimated to within a few percent of its actual measured value without danger by the use of a graded submaximal exercise tolerance test. This is the exercise test carried out in a fitness test protocol described hereinabove. In fact, by plotting maximal oxygen uptake level $VO_{2max}$ against the duration of exercise, in minutes, the Van der Walt relation results, in which $VO_{2max}$ can be determined for any particular duration:

If the subject 10 is male, the maximal oxygen uptake $VO_{2max}$ is calculated:

$VO_{2max} = 3.83T + 13$, if T is between zero and seven minutes, and $VO_{2max} = 2.33T + 24$, where T is between seven and eighteen minutes.

Here, T is expressed in minutes and $VO_{2max}$ is expressed in milliliters of oxygen per kilogram of body weight per minute. Maximal oxygen uptake $VO_{2max}$ is expressed in these units, and is so displayed, regardless whether U.S. or metric units are selected. If the subject 10 is female, a multiplicative factor of 0.875 is used to yield the correct result for $VO_{2max}$. Once the value for the maximal oxygen uptake $VO_{2max}$ is automatically calculated, the resulting value is displayed in ZONE 4, and is stored in the memory 55a to be used as a fitness index and for reference in guiding the subject's exercise training.

The following table shows a comparison of actual and calculated values of $VO_{2max}$ for individuals reaching exhaustion at the end of the various three minute intervals. As is apparent, the correlation between actual $VO_{2max}$ values and the values calculated using data from the submaximal exercise stress tolerance test is extremely good.

| SPEEDS | | | ACTUAL | ESTIMATED $VO_{2max}$ (From Exercise |
|---|---|---|---|---|
| MPH | KM/HR. | TIME | $VO_{2max}$ | Test) |
| 4 | 6.54 | 3 MIN. | 31.8 | 31.0 |
| 6 | 9.72 | 3 MIN. | 37.9 | 38.0 |
| 8 | 12.96 | 3 MIN. | 46.4 | 46.6 |
| 10 | 16.20 | 3 MIN. | 57.4 | 59.0 |
| 12 | 19.44 | 3 MIN. | 70.6 | 70.4 |
| 14 | 22.68 | 3 MIN. | 86.6 | 82.0 |

Once the test protocol is complete, the monitor device 11 can be set into a "pacer" mode by depressing the PACE key 14. A selected speed V can be set by use of the key 18. This causes the microprocessor 55 to provide the alarm signals ALM for pacing the subject 10 at a stride frequency corresponding to the selected running velocity V chosen by the subject or the subject's coach or trainer. The alarm signals ALM produce the pacer tones at a "normal" pitch as long as the subject's heart rate $HR_E$ stays within a range such that the exercise stress level (%$VO_{2max}$) is between 60% and 80%.

The pacer tones are provided at a higher pitch if the stress level (%$VO_{2max}$) is above 80%, and at a lower pitch if the stress level (%$VO_{2max}$) is below 60%. This achieves an optimal submaximal training effect by permitting the subject to exercise, for example, for 20 to 30 minute periods on an alternate day basis at work loads corresponding to 60 to 80 percent of $VO_{2max}$.

A well-established linear relationship exists between the percent of $VO_{2max}$ required for a given workload, and the heart rate achieved at that work load, so that the heart rate corresponding, e.g., to 70 percent of maximal oxygen uptake level $VO_{2max}$ can be easily calculated from the relationship:

$$(\% \ VO_{2max}) = \frac{HR_E - HR_R + 10}{HR_M - HR_R} \quad (1)$$

In this relationship, the left hand expression (%$VO_{2max}$) corresponds to a percentage value up to one hundred percent, $HR_E$ is the heart rate at that given level of exercise, and $HR_R$ and $HR_M$ are the resting heart rate and maximal heart rate as determined during the test protocol.

The alarm signals ALM can be provided, for example, at 1.5 KHz for pacing signals (pacer tones) in the training range. However, where the exercise heart rate $HR_E$ drops to or below a level corresponding to a effort level of 60 percent level for (%$VO_{2max}$), or rises above a                         for percent level max), the tone can change to indicate an alarm condition. For example, a higher pitch pacer tone indicates that the subject 10 is above the training range and should slow down, as necessary, to maintain his speed within the training range of 60 to 80 percent. A lower pitch pacer tone indicates the subject heart rate $HR_E$ is below a stress level (%$VO_{2max}$) of 60 percent. The pacer tones continue at the prescribed stride frequency SF for a selected speed V even when the heart rate is elevated above the 80% level, but the pitch of the tone serves to warn the subject that he is perhaps exercising at a hazardous pace.

The alarm signals ALM provide warning tones any time the sensor 12 is connected if the heart rate $HR_E$ corresponds to a value (%$VO_{2max}$) outside the range of 60% to 80%. This is true even when not in the pacer mode. However, in the pacer mode, the warning tones are superimposed onto the pacer tones.

In order to establish the pacing cadence SL for the signal ALM used for the pacing tones, and to pace the individual subject 10 accurately for any of various speeds, the individual's stride length SL must be known. It has been shown that the subject's running stride length SL is function of both leg length L (in meters) and running speed V (in kilometers per hour), according to the following relationship $$SL = 0.598 + 0.881V + 0.720L \quad (2)$$

The leg length L of an individual is a generally linear function of the person's height, and can be expressed as follows:

$$L = 0.745H - 0.250 \quad (3)$$

where both the leg length L and the height H are expressed in meters.

Therefore, for use in the pacer function mode, the stride length SL is automatically determined from the height H of the subject 10, as follows:

$$SL = -0.778 + 0.881V + 0.5364H \quad (4)$$

The subject's effective running speed V, or speed equivalent of other training, is determined from his or her heart rate and fitness data.

First of all, the stored value of $VO_{2max}$ is recalled from memory. Then, this value is multiplied by the weight M (in kilograms) of the subject 10 and is again divided by a factor of 1000 to normalize the subject's maximum actual exercise oxygen uptake $VO_2$ in units of liters of oxygen per minute. This is multiplied by X% to correspond to the stress level, or percent of maximal oxygen uptake (%$VO_{2max}$), as determined in equation (1).

The running speed corresponding to this particular exercise stress level is then expressed as follows:

$$V = \sqrt{\frac{\frac{X\% \times VO_2}{M} + \frac{0.419}{M} - 0.03257}{0.000117}} \quad (5)$$

where speed V is expressed in kilometers per hour, $VO_2$ is expressed in liters per minute, and M is expressed in kilograms. This value for V can be used in the equation (4) above for determining stride length SL. The value for V calculated using the equation (5) is displayed in ZONE 4 of the display 13, and is used to calculate distance based on exercise stress and fitness level of the subject 10, and gives values of exercise equivalency for exercise training other than running, e.g., swimming, tennis, calisthenics, etc.

It can be seen that equation (5) can be simplified to the following relationship:

$$V = \sqrt{\frac{X\% \times VO_{2max} + \frac{0.419}{M} - 0.03257}{0.000117}} \quad (5a)$$

The importance of taking running speed into account for the calculation of stride length SL can be shown by the significant different in stride length when running at four or at twelve miles per hour. For example, at a running speed of four miles per hour (i.e., 15 minutes per mile or 6.5 Km/hour), the stride length SL is 0.76 meters. However, at a running speed of twelve miles per hour (5 minutes per mile or 19.4 Km/hour) the stride length SL is 1.9 meters.

A stride frequency SF is then provided for the particular running speed V, which can be determined according to equation (5) above, as expressed in equation (6):

$$SF = \frac{V \times 1000}{SL \times 3600} \quad (6)$$

where SF is expressed in strides per second, V in kilometers per hour, and SL in meters.

The cadence SF used for the test protocol or exercise training can then be provided at the stride frequency SF for a given running speed V. For exercise training, this cadence can be calculated automatically at a desired training speed, e.g., 7 minutes per mile, using the subject's stride length SF. The subject 10 can establish a pace at a given fixed speed V, regardless of the corresponding oxygen uptake level. This can be done by depressing the PACE key 14 and the PROGRAM and ENTER/MEMO keys 18, 19 as appropriate with the desired speed V appearing (e.g., in minutes per mile) in the display in ZONE 4.

The algorithm necessary to carry out the above pacing function would involve only the foregoing equations (4) and (6), and the details thereof need not be discussed in detail.

If there is sufficient memory capacity in the microprocessor 55, the stride frequencies SF for the various speeds V used during the submaximal exercise test protocol can also be calculated using equations (4) and (6), although this is not critical. This protocol can be carried out effectively using approximate stride frequencies not tailored to the subject's height H.

As has been mentioned previously, any given exercise heart $HR_E$ corresponds to a particular percentage of the subject's maximal oxygen uptake rate $VO_{2max}$. Thus, by storing the maximum oxygen uptake rate $VO_{2max}$ and the weight M of the subject 10, and also by continuously calculating the percentage oxygen uptake (%$VO_{2max}$) based on the continuously measured exercise heart rate $HR_E$, and the stored maximal and resting heart rates $HR_M$ and $HR_R$, the total oxygen consumption during training can be calculated. That is, the value for the exercise heart rate $HR_E$ can be transformed to the quantity of oxygen consumed per minute. Because the oxygen consumption is proportional to the calorie expenditure at the rate of 200 ml of oxygen for each calorie, the number of calories consumed per minute can be readily determined. The resulting quantity is stored in the microprocessor memory 55a. That is, the number of calories CAL for each minute of exercise can be determined according to the following relationship $$CAL = \frac{VO_{2max} \times (\% \, VO_{2max}) \times M}{0.2} \quad (7)$$

Then, by merely accumulating the value CAL in the memory 55a at one minute intervals, the total caloric consumption CAL for an exercise session can be determined.

After a session of exercise training, the subject 10 can determine his or her recovery rate by depressing the RECOVERY TIME time key 17 immediately after completing a training run. Then, the time display in ZONE 2 clears, and count the number of minutes, second, and tenths of a second required for the subject's heart rate $HR_E$ to return to a value of 100 BPM, and the clock face graphic 34 appears in ZONE 1 of the display 13. The time shown on the display in ZONE 2 will automatically halt when 100 BPM is reached.

The recovery rate provides an additional index of fitness, as it indicates the rapidity at which the subject's cardiovascular system can replenish oxygen to the body following heavy exercise.

The FUNCTION push-button key 15 is used to display of heart rate, distance covered, running speed, or calories consumed on the digits in ZONE 4. Successive depressions of the function key 15 causes the display 13 to cycle through the heart rate, distance, speed, and calories-consumed modes.

In the heart-rate mode, the graphic display 33 appears in ZONE 1, and a visual display of the exercise heart rate $HR_E$ appears in ZONE 4 and is updated every six beats or ten seconds. In this mode, if the RUN/PAUSE key 16 is depressed, warning beeps or tones will be provided if the heart rate $HR_E$ goes outside the 60 percent to 80 percent range of maximal oxygen uptake $VO_{2max}$.

A successive depression of the FUNCTION key 15 brings on the distance mode, and causes the graphic 46 to be displayed. The distance, in miles or kilometers, as appropriate, appears in ZONE 4. This value is computed using the value V calculated using equation (5). The memory 55a accumulates the value V for periodic intervals of time, favorably each ten seconds.

A successive depression of the FUNCTION key 15 brings about the speed mode and causes the runner stick-figure graphic 47 to appear in ZONE 3 and the running speed V to be displayed in ZONE 4. This value is favorably expressed in minutes per mile, or minutes per kilometers, as appropriate. If the heart rate monitor device 11 is used for exercise other than running (e.g., swimming) this value corresponds to the exercise equivalent of running, in minutes per mile, or per kilometer.

If the bicycle sensor 65 is plugged into the appropriate socket, the bicycle wheel graphic 35 appears, and the speed is displayed in ZONE 4 corresponds to the bicycle speed, in miles per hour or kilometers per hours, as appropriate, as calculated in a fashion to be described later.

Another depression of the function key 15 causes the ice-cream-cone graphic 48 to appear, and the total calories consumed, as determined as described above, is displayed in ZONE 4.

Following this, a further depression of the FUNCTION key 15 brings the display 13 back to the heart rate mode.

It is preferred that the warning tones be provided at any time that the heart sensor 12 is properly plugged in, and the exercise heart rate is such as to correspond to an exercise level either below 60 percent or above 80 percent of $VO_{max}$. Also, the graphic display 36 should flash on and off for each heart beat, when the heart beat sensor 12 is properly attached and worn on the subject 10, and the POWER key 21 has been depressed to turn the device on.

When the bike sensor 65 is connected, the graphic display 35 is continuously shown. The diameter of the bicycle wheel must be entered, to appear in ZONE 4, using the keys 18 and 19. Then, calculation of speed, distance, and calories consumed is determined using the value of the wheel circumference, rather than stride length SL. Of course, in the bicycle mode pacing tones are not necessary, as the cycling speed is indicated on the display in ZONE 4. Since the sensor pulses BS are provided at a rate of, for example, one pulse per revolution, the cycling speed can be computed directly in the microprocessor 55 from the time required for each revolution and the circumference of the wheel.

The above embodiment is, of course, an example of many possible systems using the principles of this invention.

In another embodiment, an additional output jack provides a system output in addition to what is shown on the display 13. This would permit medical adaption by means of a tape recorder, electrocardiogram (EKG) machine, or telemetry unit to be plugged into the device. The subject's stress level can be monitored by a physician or other trained medical professional.

In yet another embodiment, using a different microprocessor 55, the stop watch or chronometer has a separate lap timer, giving a "split-time" capability.

In still another version, a larger memory capacity permits the subject's age to be entered, so that the maximum heart rate $HR_M$ can be automatically determined.

In yet another version, any change of the sex, weight M, height H, or resting heart rate $HR_R$ clears the protocol memory so that the test protocol sequence is initiated.

A voice synthesis unit can be incorporated into the device, or connected to it as an add-on feature, to give audible indications of $VO_{2max}$, stress level, running speed, distance, or calories consumed.

A watertight case can be provided for the device, with plugs fitting the sockets on the device and watertight depressors for actuating the various keys 14–22. The sensor(s) can be plugged into sealable sockets on the watertight case, with an O-ring seal on the sensor plug achieving a watertight seal. This makes the device suitable for use in monitoring the training of a swimmer.

While a preferred embodiment of this invention has been described in detail hereinabove, it is apparent that many modifications and variations thereof will be apparent to those of ordinary skill in the art without departure from the scope and spirit of this invention, as defined in the appended claims.

We claim:

1. In a personal fitness level monitor system for monitoring fitness parameters of an animate subject as a function of heat rate during exercise training, of the type comprising heart beat sensor means worn on said animate subject to sense said subject's heart beat; data entry means for entering selected data peculiar to said subject; display means for displaying said entered selected data and one or more fitness parameters calculated on the basis of said entered selected data and the detected heart beats of said subject; and microprocessor means for storing said entered data and calculations exercise heart rate HRE from said detected heart beats and calculating said one or more fitness parameters based on the entered data and heart rate data, said system including timing means for use in measuring the heart rate of the subject on the basis of said detected heart beats; and indicator means providing an indication to said subject of the level of training exercise; the improvement wherein said fitness parameters include a maximal oxygen uptake parameter $VO_{2max}$ as a fitness index; and said microprocessor means includes:

(1) means for establishing an exercise protocol in which the subject exercises at a first relatively low effort level for a first period, and at progressively higher effort levels for corresponding successive periods, means for continuously measuring the heart rate in said microprocessor means based on said detected heart beat of said subject while the latter is exercising at each of said effort levels according to said protocol;

(2) means for halting the exercise protocol when the exercise heart rate HRE of said subject reaches a maximum heart rate $HR_M$ predetermined from said selected data, and means for storing the maximum heart rate $HR_M$ and elapsed time T from the commencement of said exercise protocol until said maximum heart $HR_M$ rate is attained;

(3) means for calculating and storing said fitness index according to a relationship $$VO_{2max} = aT + b$$

where a and b are experimentally derived coefficients; and (4) means for causing said display means to display the calculated fitness index $VO_{2max}$.

2. The fitness monitor system of claim 1 wherein said means for establishing an exercise protocol includes means for pacing said subject to exercise at levels corresponding to running speeds as shown in the following chart for the indicated successive intervals:

| speeds | successive intervals |
|---|---|
| 4 miles per hour | first three minutes |
| 6 miles per hour | next three minutes |
| 8 miles per hour | next three minutes |
| 10 miles per hour | next three minutes |
| 12 miles per hour | next three minutes |
| 14 miles per hour | next three minutes; | and said means for calculating includes means for computing said fitness index $VO_{2max}$ according to the following relationships:

$VO_{2max} = 3.83T + 13$, when T is between 0 and 7 mintues and $VO_{2max} = 2.33T + 24$, when T is between 7 and 18 minutes, T being the number of minutes and $VO_{2max}$ being expressed in units of milliliters of oxygen per kilogram per minute.

3. The fitness monitor system of claim 2, wherein said data entry means includes means to enter said subject's sex as said selected data, and said means for calculating is adapted to multiply the fitness index $VO_{2max}$ by an adjustment factor according to the subject's sex.

4. The fitness monitor system of claim 1, wherein said microprocessor means includes means for measuring, by means of said heart beat sensor means and said timer means, the heart rate of said subject while at rest and storing the same in said microprocessor means as a resting heart rate $HR_R$, and said microprocessor means includes means for calculating, while the subject is exercising, the fraction of maximum oxygen uptake ($\%VO_{2max}$) in accordance with the relationship $$(\% VO_{2max}) = \frac{HR_E - HR_R + C}{HR_M - HR_R}$$

where C is a predetermined constant; and said indicator means includes means for indicating as exercise stress level said calculated fraction of maximum oxygen uptake ($\%VO_{2max}$).

5. The fitness monitor system of claim 4, wherein $C=10$.

6. The fitness monitor system of claim 4, wherein said means for establishing includes audible tone generating means for providing tones having a first pitch when said subject's exercise heart rate $HR_E$ is such that said fraction ($\%VO_{2max}$) is within a predetermined training range; and means for indicating said fraction includes means for changing the pitch when said fraction ($\%VO_{2max}$) is above or below said range.

7. The fitness monitor system of claim 1, wherein said data entry means includes means for entering the height H of said subject, and said means for establishing includes means for establishing a particular effort level by calculating a running cadence SF corresponding to a desired running speed V by dividing a predetermined stride length SL of said subject by the desired running speed V, and wherein said microprocessor means includes means for calculating the predetermined stride length SL as a function of the height H of the subject and of the desired running speed V to satisfy a relation $SL = g + hV + jH$, where g, h, and j are predetermined coefficients; and said indicator means includes audible tone generator means coupled to said means for establishing for generating pacer tones as pulses at said cadence SF.

8. The fitness monitor device of claim 7, wherein said means for calculating said stride length SL includes means for calculating the stride length SL according to the relation $SL = 0.778 + 0.881V + 0.5364H$ where SL and H are in meters and V is in KM per hour.

9. A method of monitoring the oxygen uptake capacity of a human subject during exercise training wherein heart beat sensor means are worn on said subject to sense said subject's heart beat wherein selected data peculiar to said subject including the subject's height H, weight M, and gender are employed; and wherein a maximal oxygen uptake parameter $VO_{2max}$ is calculated as a fitness index; the method comprising the steps of (1) recording the weight M, height H, and gender of the subject as said selected data;

(2) measuring the heart rate of said subject while at rest and recording such heart rate as a resting heart rate $HR_R$;

(3) establishing an exercise protocol for said subject at a rate that varies according to a prescribed protocol in which said exercise effort level gradually increases, and continuously measuring the exercise heart rate HRE of the subject while exercising according to said protocol;

(4) halting the exercise protocol when the exercise heart rate $HR_E$ attains a maxium heart rate $HR_M$ predetermined from the data recorded in step (1), and recording the maximum heart rate $HR_M$ and elapsed time T from the commencement of said exercise protocol until said maximum heart rate $HR_M$ is attained; and (5) calculating said fitness index according to the relationship $VO_{2max} = aT + b$ where a and b are experimentally derived coefficients.

10. The method of claim 9 wherein said exercise protocol includes the step of causing the subject to run at speeds V1-6 as

| speeds | successive intervals |
|---|---|
| $V_1$ | first three minutes |
| $V_2$ | next three minutes |
| $V_3$ | next three minutes |
| $V_4$ | next three minutes |
| $V_5$ | next three minutes |
| $V_6$ | next three minutes; and | wherein the step of calculating includes the step of computing said fitness index according to the relationships:

$VO_{2max} = 3.83\ T + 13$, where T is between 0 and 7 minutes and said gender is male;

$VO_{2max} = 2.33\ T + 13$, where T is between 7 and 18 minutes and said gender is male;

$VO_{2max} = (3.83\ T + 13) \times 0.875$ where T is between 0 and 7 minutes and said gender is female; and $VO_{2max} = (2.33\ T + 13) \times 0.875$ where T is between 7 and 18 minutes and said gender is female;

T being the number of minutes and $VO_{2max}$ being expressed in milliliters of oxygen per kilogram per minute.

11. The method of claim 10, wherein said speeds $V_1$ to $V_6$ are respectively 4, 6, 8, 10, 12, and 14 miles per hour.

12. The method of claim 10, further comprising calculations an exercise stress level ($\%VO_{2max}$) for said subject during exercise training based on the subject's exercise heart rate $HR_E$, such calculation following the relation:

$$(\%\ VO_{2max}) = \frac{HR_E - HR_R + f}{HR_M - HR_R}$$

where f is a predetermined constant; and displaying a training fitness parameter based on said exercise stress level.

13. The method of claim 12, further comprising, and the step of computing the quantity of colonies consumed during exercise CAL according to the relation:

$$CAL = \frac{VO_{2max} \times (\%\ VO_{2max}) \times M \times T}{200}$$

where T is the elapsed time in minutes and M is expressed in kilograms.

14. The method of claim 13 wherein said step of computing CAL includes the step of periodically calculations CAL during a predetermined interval and adding the result to that calculated in previous intervals.

15. The method of claim 9, wherein the step of establishing includes indications providing pulsed audio tones each representing a step at a running cadence SF corresponding to a desired running speed V.

16. The method of claim 15, wherein said running cadence SF determined for each running speed V by dividing the running speed V by the subject's stride length SL; and said stride length SL is determined from, the subject's height H and running speed V according to the relationship $$SL = c + dv + eH,$$

where c, d, and e are predetermined coefficients.

17. The method of claim 9 wherein said step of establishing an exercise protocol includes the step of causing the subject to exercise on a cycle at gradually increasing effort levels until said step of halting.

* * * * *